(12) United States Patent
Stengelin et al.

(10) Patent No.: US 6,180,618 B1
(45) Date of Patent: Jan. 30, 2001

(54) PROPANOLAMINE DERIVATIVES LINKED TO BILE ACIDS, PROCESSES FOR THEIR PREPARATION, PHARMACEUTICALS COMPRISING THESE COMPOUNDS, AND THEIR USE

(75) Inventors: Siegfried Stengelin, Eppstein; Alfons Enhsen, Büttelborn; Heiner Glombik, Hofheim; Werner Kramer, Mainz-Laubenheim; Eugen Falk, Frankfurt, all of (DE)

(73) Assignee: Aventis Pharma Deutschland GmbH, Frankfurt am Main (DE)

( * ) Notice: Under 35 U.S.C. 154(b), the term of this patent shall be extended for 0 days.

(21) Appl. No.: 09/408,169

(22) Filed: Sep. 29, 1999

(30) Foreign Application Priority Data

Oct. 2, 1998 (DE) ................................. 198 45 403

(51) Int. Cl.[7] .............................. A61K 31/58; C07J 43/00
(52) U.S. Cl. .......................... 514/176; 540/107; 540/109; 540/112; 540/113
(58) Field of Search ..................... 540/107, 109, 540/112, 113; 514/176

(56) References Cited

U.S. PATENT DOCUMENTS

| 5,045,567 | 9/1991 | Kienzle . |
| 5,250,524 | 10/1993 | Kramer et al. . |
| 5,610,151 | 3/1997 | Glombik et al. . |

FOREIGN PATENT DOCUMENTS

| 2123050 | 11/1994 | (CA) . |
| 0 345 591 A1 | 12/1989 | (EP) . |
| 0 489 423 A1 | 6/1992 | (EP) . |
| 0 624 593 A2 | 11/1994 | (EP) . |
| 0 869 121 A1 | 10/1998 | (EP) . |
| 04266822 | * 9/1992 | (JP) . |

OTHER PUBLICATIONS

English Abstract, Derwent No. 89–365388, 1989.
English Abstract, Derwent No. 92–193618, 1992.
English Abstract, Derwent No. 94–350741, 1994.
English Abstract, Derwent No. 98–508454, 1998.

* cited by examiner

*Primary Examiner*—Barbara Badio
(74) *Attorney, Agent, or Firm*—Finnegan, Henderson, Farabow, Garrett and Dunner, L.L.P.

(57) ABSTRACT

Compounds of formula (I)

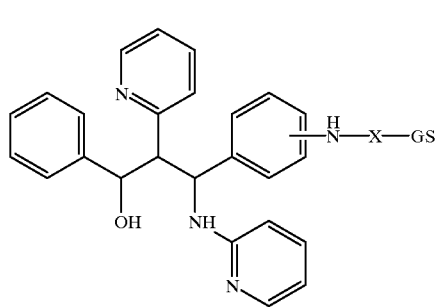

in which the radicals are as defined in the specification and claims, and physiologically tolerated and physiologically functional derivatives thereof and processes for their preparation are described. The compounds are suitable, for example, as hypolipidemic agents.

11 Claims, No Drawings

PROPANOLAMINE DERIVATIVES LINKED TO BILE ACIDS, PROCESSES FOR THEIR PREPARATION, PHARMACEUTICALS COMPRISING THESE COMPOUNDS, AND THEIR USE

Under the provisions of Section 119 of 35 U.S.C., Applicants hereby claim the benefit of the filing date of Federal Republic of Germany Patent Application Number 19845403.1, filed Oct. 2,1998, which Application is hereby incorporated by reference.

The present invention relates to novel substituted propanolamine derivatives, their pharmaceutically tolerated salts, their physiologically functional derivatives, and the preparation and use of such derivatives and salts.

Several classes of active compounds have been described for treatment of adiposity and disturbances in lipid metabolism, e.g., polymeric adsorbers, such as cholestyramine, benzothiazepines (WO 93/16055), bile acid dimers and conjugates (EP 0 489 423), and 4-amino-2-ureido-pyrimidine-5-carboxamides (EP 0 557 879).

The present invention was based on the need to provide further compounds with therapeutically valuable hypolipidemic action.

The present invention therefore relates to compounds of formula (I)

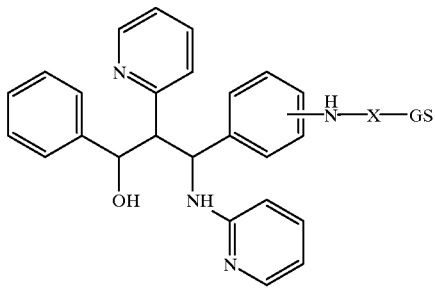

wherein:
GS is a bile acid group of the formula

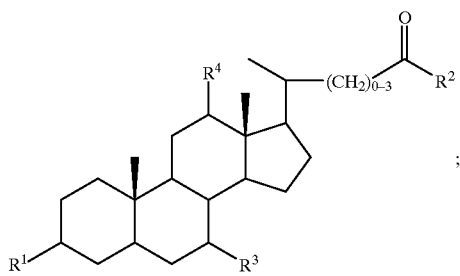

$R^1$ is a bond to X or —OH;

$R^2$ is a bond to X, —OH, —O—($C_1$-$C_6$)-alkyl, —NH—($C_2$-$C_6$)-alkyl-$SO_3H$, —N($CH_3$)—$CH_2$—$CH_2$—$SO_3H$, —NH—($C_1$-$C_6$)-alkyl-COOH, or —N($CH_3$)—($C_1$-$C_6$)-alkyl-COOH;

with the proviso that $R^1$ and $R^2$ can not simultaneously be a bond to X;

$R^3$, $R^4$ each independently of one another is H or OH;

or a bond;

l, m, n each independently of one another is 0 or 1;

L is —($C_1$-$C_6$)-alkyl or phenyl;

$AA_1$, $AA_2$ each independently of one another is an amino acid radical or an amino acid radical which is mono or polysubstituted by an amino acid-protective group;

and pharmaceutically tolerated salts and physiologically functional derivatives thereof.

Preferred compounds of formula (I) are those in which one or more radical(s) has or have the following meaning:
GS is a bile acid group of the formula

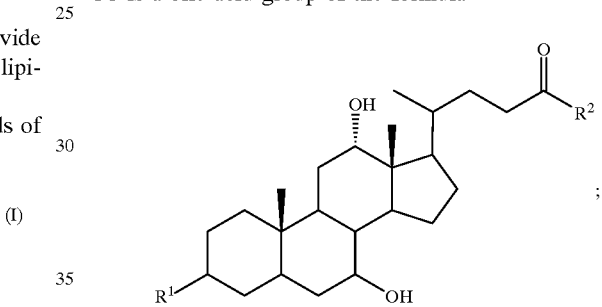

$R^1$ is a bond to X or OH;

$R^2$ is a bond to X, —OH, —O—($C_1$-$C_6$)-alkyl, —NH—($C_2$-$C_6$)-alkyl-$SO_3H$, —N($CH_3$)—$CH_2$—$CH_2$—$SO_3H$, —N H—($C_1$-$C_6$)-alkyl-COOH, or —N($CH_3$)—($C_1$-$C_6$)-alkyl-COOH;

with the proviso that $R^1$ and $R^2$ can not simultaneously be a bond to X;

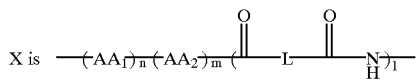

or a bond;

l, m, n each independently of one another is 0 or 1;

L is —($C_1$-$C_6$)-alkyl or phenyl;

$AA_1$, $AA_2$, each independently of one another is an amino acid radical or an amino acid radical which is mono- or polysubstituted by an amino acid-protective group;

and pharmaceutically tolerated salts and physiologically functional derivatives thereof.

In certain currently preferable embodiments, compounds of formula (I) are those in which one or more radical(s) has or have the following meaning:

GS is a bile acid group of the formula

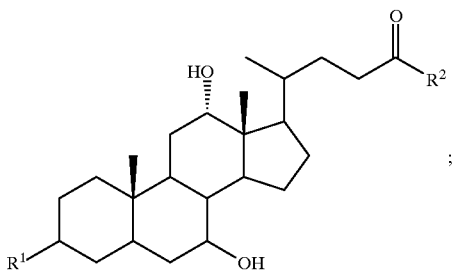

$R^1$ is a bond to X or —OH;
$R^2$ is a bond to X, —OH, —O—$(C_1-C_6)$-alkyl, —NH—$(C_2-C_6)$-alkyl-$SO_3H$, or —NH—$(C_1-C_6)$-alkyl-COOH;
with proviso that $R^1$ and $R^2$ can not simultaneously be a bond to X;

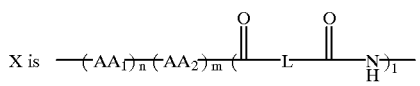

or a bond;
l, m, n, each independently of one another is 0 or 1;
L is —$(C_1-C_6)$-alkyl;
$AA_1$, $AA_2$, each independently of one another is an amino acid radical or an amino acid radical which is mono- or polysubstituted by an amino acid-protective group;
and pharmaceutically tolerated salts thereof.

The term alkyl is understood as meaning straight-chain or branched hydrocarbon chains.

The term amino acids or amino acid radicals indicates the stereoisomeric forms, i.e., D- or L-forms, of any of the following compounds:

| | | |
|---|---|---|
| alanine | glycine | proline |
| cysteine | histidine | glutamine |
| aspartic acid | isoleucine | arginine |
| glutamic acid | lysine | serine |
| phenylalanine | leucine | threonine |

| | |
|---|---|
| tryptophan | methionine valine |
| tyrosine | asparagine |
| 2-aminoadipic acid | 2-aminoisobutyric acid |
| 3-aminoadipic acid | 3-aminoisobutyric acid |
| beta-alanine | 2-aminopimelic acid |
| 2-aminobutyric acid | 2,4-diaminobutyric acid |
| 4-aminobutyric acid | desmosine |
| piperidic acid | 2,2-diaminopimelic acid |
| 6-aminocaproic acid | 2,3-diaminopropionic acid |
| 2-aminoheptanoic acid | N-ethylglycine |
| 2-(2-thienyl)-glycine | 3-(2-thienyl)-alanine |
| penicillamine | N-methylglycine |
| N-ethylasparagine | N-methylisoleucine |
| hydroxylysine | 6-N-methyllysine |
| allo-hydroxylysine | N-methylvaline |
| 3-hydroxyproline | norvaline |
| 4-hydroxyproline | norleucine |
| isodesmosine | ornithine |
| allo-isoleucine | 11-aminoundecanoic acid |

The amino acids are abbreviated in accordance with customary nomenclature (e.g., Schröder, Lübke, *The Peptides*, Volume I, New York 1965, pages XXII–XXIII; Houben-Weyl, *Methoden der Organischen Chemie* (*Methods of Organic Chemistry*), Volume XV/1 and 2, Stuttgart 1974). The amino acid D-Asp is the D-form of aspartic acid. Peptides are acid amides from their chemical nature and dissociate into amino acids on hydrolysis.

The term amino acid-protective groups is to be understood to mean suitable groups which protect the functional groups of the side chains of the amino acid radicals (see, e.g., T. W. Greene, P. G. M. Wuts, *Protective Groups in Organic Synthesis*, 2nd Ed., John Wiley and Sons, New York 1991). Often utilized amino acid-protective groups are, for example, t-butyloxy-carbonyl (BOC), 9-fluorenylmethoxy-carbonyl (Fmoc), benzyloxy-carbonyl (Z), 2-(3,5-dimethoxyphenyl)prop-2-yloxycarbonyl (Ddz), methyl, t-butyl, trityl and S-t-butyl, and t-butylamino-carbonyl.

The present invention furthermore relates to processes for the preparation of compounds of formula (I) which proceed according to the following reaction equations (equations 1 to 4):

Process A

Equation 1

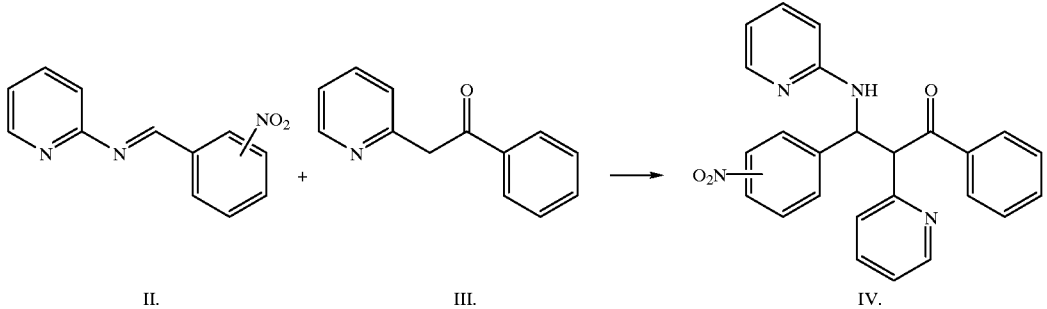

II.     III.     IV.

1. reduction
2. separation of isomers

-continued

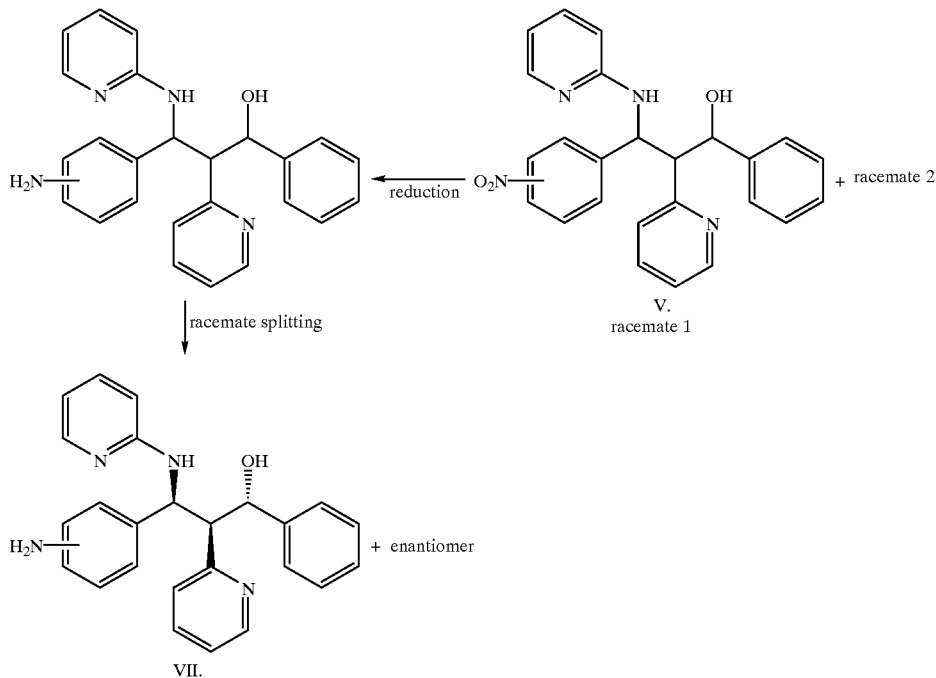

V.
racemate 1

VII.

Compounds of type IV are obtained by reacting o-, m- or p-substituted imines of type 11 with ketone III. The reaction can be carried out, e.g., by mixing the two compounds in bulk without a solvent and then heating, or with a suitable solvent, such as ethanol, tetrahydrofuran (THF), toluene, diglyme or tetradecane, at temperatures of from 20° C. to 150° C.

The keto compounds of type IV are reduced to hydroxy compounds of type V with $NaBH_4$ or another suitable reducing agent in a suitable solvent, e.g., methanol, THF or THF/water, at temperatures between −30° C. and +40° C. Two isomer mixtures (racemates) are usually obtained as the main product in the reduction. The various racemates can be separated from one another by fractional crystallization or silica gel chromatography. The nitro group in compounds of type V can be reduced by known processes, e.g., catalytic hydrogenation with Pd or Pd-on-charcoal and $H_2$ in methanol.

The racemic compounds of type VI thus obtained can be separated further into their enantiomers. The racemate splitting of VI into enantiomers of type VII can be carried out by chromatography over chiral column material or by processes known from the literature using optically active auxiliary reagents (*J. Org. Chem.* 44, 1979, 4891).

Equation 2

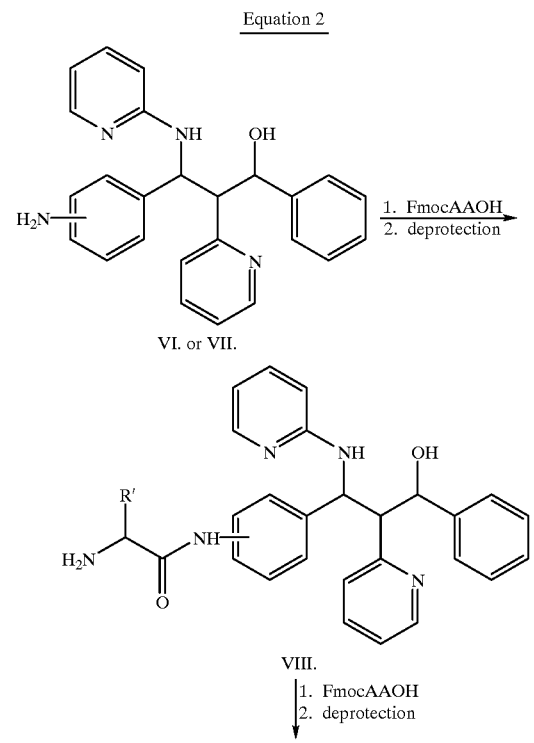

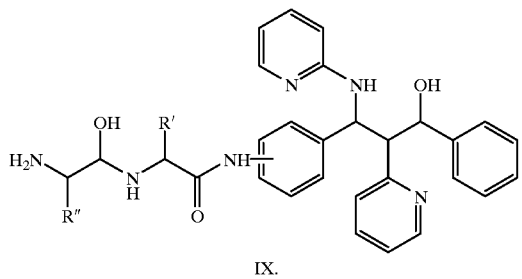

IX.

In accordance with equation 2, the aromatic amines of type VI or VII (as a racemate or as a pure enantiomer) can be reacted with an amino acid by known standard peptide coupling processes to give derivatives VIII. A suitable process is coupling with TOTU and triethylamine in DMF.

Literature examples are illustrated in, e.g., G. Breipohl, W. König EP 0460446, W. König, G. Breipohl, P. Pokorny, and M. Birkner, in E. Giralt and D. Andreu (Eds.) *Peptides* 1990, Escom, Leiden, 1991, 143–145. The radicals $AA_1$ and $AA_2$ have the meanings given according to formula (I). The amino function of the amino acid is provided with a protective group such as Fmoc, and the carboxylic acid is unprotected.

In amino acids with side chain functional groups, the functional groups are protected accordingly, either temporarily during the synthesis, or throughout the synthesis of the compounds according to the present invention.

To arrive at derivative VIII, the protective group of the amino function is split off. In the case of Fmoc, this is accomplished in a mixture of DMF and piperidine. Dipeptide conjugates IX are obtained if, starting from compounds of type VIII, the reaction sequence (a) coupling of an amino acid and (b) deprotection is repeated.

Equation 3

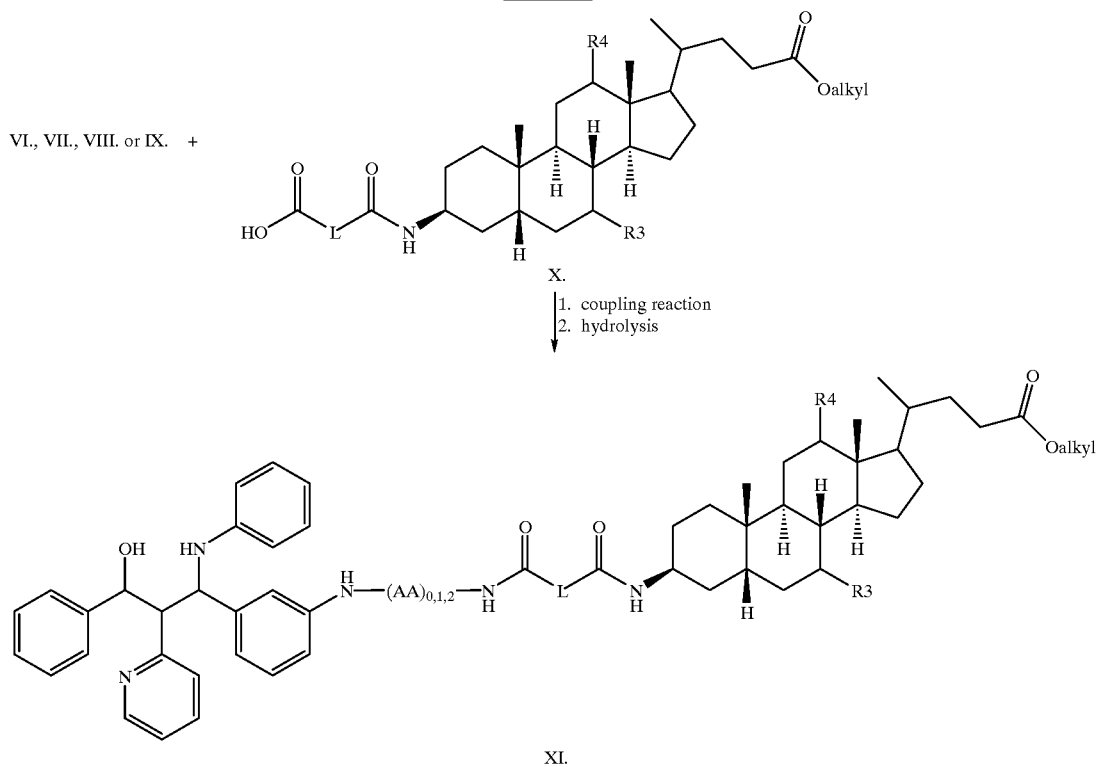

Bile acid derivatives of type X can be prepared from 3-amino-bile acid esters by linking with alkyl- or aryidicarboxylic acids or derivatives thereof, such as succinic anhydride, by known processes, see EP 0614908 and EP 0489423. The compounds X are reacted with amino compounds of type VI, VII, VIII or IX by standard peptide coupling processes. After the coupling reaction, the compounds of type XI are obtained by hydrolysis of the alkyl ester function of the bile acid moiety.

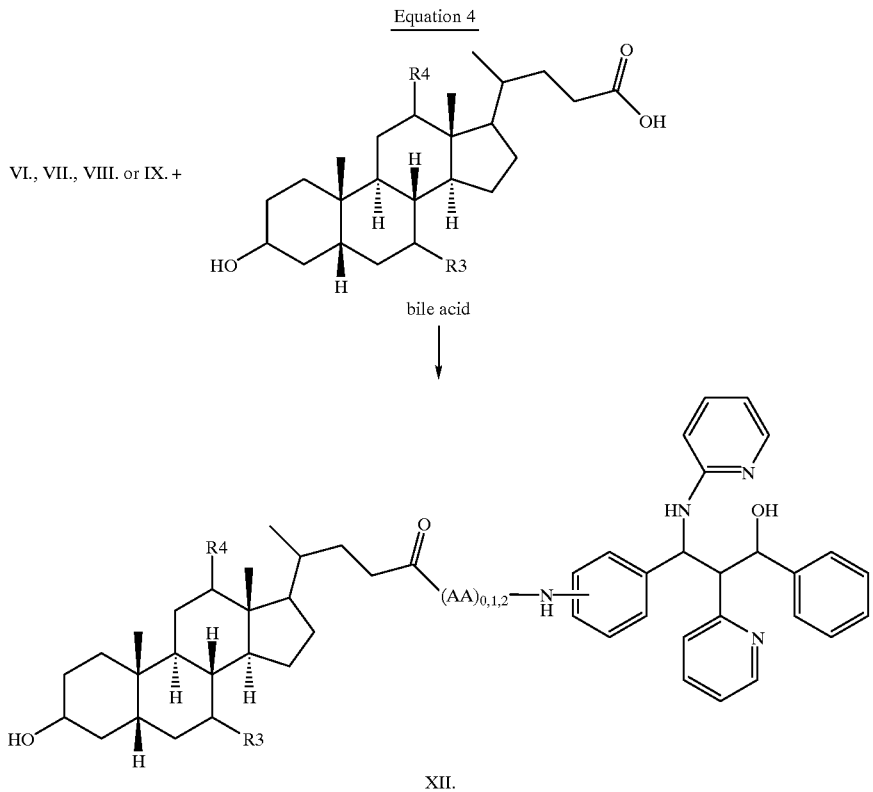

The amino compounds of type VI, VII, VIII or IX can be reached with the carboxylic acid function of bile acids. Known peptide coupling processes are likewise used here, for example, coupling in the presence of TOTU and triethylamine, or with dicyclohexylcarbodiimide, hydroxybenzotriazole and triethylamine in THF. The compounds of type XII can be obtained by this process.

Because of their higher solubility in water compared with the starting or base compounds, pharmaceutically tolerated salts are particularly suitable for medical applications. These salts must have a pharmaceutically tolerated anion or cation. Suitable pharmaceutically tolerated acid addition salts of the compounds within the scope of the present invention include salts of inorganic acids, such as hydrochloric, hydrobromic, phosphoric, metaphosphoric, nitric, sulfonic, and sulfuric acid, and of organic acids, such as acetic, benzenesulfonic, benzoic, citric, ethanesulfonic, fumaric, gluconic, glycolic, isothionic, lactic, lactobionic, maleic, malic, methanesulfonic, succinic, p-toluenesulfonic, tartaric, and trifluoroacetic acid. The chlorine salt is particularly useful for medical purposes. Suitable pharmaceutically tolerated basic salts are ammonium salts, alkali metal salts, e.g., sodium and potassium salts, and alkaline earth metal salts, e.g., magnesium and calcium salts.

Salts with a non-pharmaceutically tolerated anion are also included in the scope of the present invention as beneficial intermediate products for the preparation or purification of pharmaceutically tolerated salts and/or for use in non-therapeutic applications such as in vitro applications.

The term "physiologically functional derivative" designates any physiologically tolerated derivative of a compound of formula (I) according to the present invention, for example, an ester, which, on administration to a mammal, such as, for example, humans, is capable of forming (directly or indirectly) a compound of formula (I) or an active metabolite thereof.

Physiologically functional derivatives also include prodrugs of the compounds according to the present invention. Such prodrugs can be metabolized in vivo to a compound according to the present invention. These prodrugs may or may not be active themselves.

The compounds according to the invention can also be in various polymorphous forms, e.g., in amorphous and crystalline polymorphous forms. All the polymorphous forms of the compounds according to the present invention are included in the scope of the present invention and are a further aspect of the present invention.

All references to "compound(s) according to formula (I)" in the following relate to compound(s) of the formula (I) as described above, and to their salts, solvates and physiologically functional derivatives as described herein.

The amount of a compound according to formula (I) which is necessary to achieve the desired biological effect depends on a number of factors, such as the specific compounds chosen, the intended use, the mode of administration and the clinical condition of the patient. In general, the daily dose is in the range from 0.3 mg to 100 mg, typically from 3 mg to 50 mg, per day per kilogram of body weight, e.g., 3–10 mg/kg/day. An intravenous dose can be in the range from 0.3 mg to 1.0 mg/kg, which can suitably be administered as an infusion of 10 ng to 100 ng per kilogram per minute. Suitable infusion solutions for this purpose can comprise from 0.1 ng to 10 mg, typically from 1 ng to 10 mg per milliliter. Individual doses can comprise from 1 mg to 10 g of the active compound. Ampoules for injections can thus contain from 1 mg to 100 mg, and individual dose formulations for oral administration, such as tablets or capsules, can contain from 1.0 to 1000 mg, typically from 10 to 600 mg. In the case of pharmaceutically tolerated salts, the above weight data relate to the weight of the benzothiazepine ion derived from the salt.

For prophylaxis or treatment of the above conditions, a compound according to formula (I) can be used directly, but is normally utilized in the form of a pharmaceutical composition with a tolerated excipient. The excipient must, of course, be tolerated in the sense that it is compatible with the other constituents of the composition and is not harmful to the health of the patient. The excipient can be a solid, a liquid, or both, and in many cases is formulated with the compound in an individual dose, e.g., as a tablet, which may comprise from 0.05% to 95% by weight of the active compound. Further pharmaceutically active substances can also be present, including further compounds according to formula (I). The pharmaceutical compositions according to the present invention can be prepared by one of the known pharmaceutical methods, which essentially comprise mixing the constituents with pharmacologically tolerated excipients and/or auxiliaries.

Pharmaceutical compositions according to the present invention are those which are suitable for oral, rectal, topical, peroral (for example sublingual) and parenteral (for example subcutaneous, intramuscular, intradermal or intravenous) administration, although the most suitable mode of administration in each individual case depends on the nature and severity of the condition to be treated and on the nature of the particular compound according to formula (I) used. Coated formulations and coated sustained-release formulations are also included in the scope of the present invention. Formulations that are resistant to acid and gastric juice are generally utilized. Suitable coatings resistant to gastric juice include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration can be in the form of separate units, such as capsules, cachets, sucking tablets or tablets, each of which comprise a certain amount of a compound according to formula (I), as powders or granules, as a solution or suspension in an aqueous or non-aqueous liquid, or as an oil-in-water or a water-in-oil emulsion.

These pharmaceutical compositions can be formulated by any suitable pharmaceutical method that comprises a step in which the active compound and the excipient (which optionally includes one or more additional constituents) are brought into contact. In general, the compositions are prepared by uniform and homogeneous mixing of the active compound with a liquid and/or finely divided solid excipient, after which the product is shaped, if required. Thus, a tablet can be prepared by pressing or shaking a powder or granules of the compound, optionally with one or more additional constituents. Pressed tablets can be prepared by tableting the compound in the free-flowing form, such as a powder or granules, optionally mixed with a binder, lubricant, inert diluent and/or at least one surface-active/ dispersing agent, in a suitable machine. Shaped tablets can be prepared by shaping the pulverulent compound, which has been moistened with an inert liquid diluent, in a suitable machine.

Pharmaceutical compositions which are suitable for per-oral (sublingual) administration include sucking tablets which comprise a compound according to formula (I) with a flavoring substance, usually sucrose, and gum arabic or tragacanth, and pastilles, which comprise the compound in an inert base, such as gelatin and glycerol, or sucrose and gum arabic.

Suitable pharmaceutical compositions for parenteral administration include preferably sterile aqueous formulations of a compound according to formula (I), which are preferably isotonic with the blood of the intended recipient. These formulations are in many cases administered intravenously, although administration can also take place subcutaneously, intramuscularly or intradermally, as an injection. These formulations can be prepared by mixing the compound with water and rendering the resulting solution sterile and isotonic with blood. Injectable compositions according to the present invention in general comprise 0.1 to 5% by weight of the active compound.

Suitable pharmaceutical compositions for rectal administration are preferably in the form of single-dose suppositories. These can be prepared by mixing a compound according to formula (I) with one or more conventional solid excipients such as cacao butter, and introducing the mixture formed into a mold.

Suitable pharmaceutical compositions for topical application to the skin are preferably in the form of an ointment, cream, lotion, paste, spray, aerosol or oil. Useful excipients are Vaseline, lanolin, polyethylene glycols, alcohols and combinations of two or more of these substances. The active compound is in general present in a concentration of 0.1 to 15% by weight of the composition, for example 0.5 to 2%.

Transdermal administration is also possible. Suitable pharmaceutical compositions for transdermal applications can be in the form of individual patches that are suitable for long-term close contact with the epidermis of the patient. Such patches suitably comprise the active compound in an optionally buffered aqueous solution, dissolved and/or dispersed in an adhesion promoter or dispersed in a polymer. A suitable active compound concentration is from about 1% to 35%, in certain embodiments, from about 3% to 15%. In certain currently preferable embodiments, the active compound can be released by electroporation or iontophoresis, as described in Pharmaceutical Research, 2(6): 318 (1986).

The present invention relates to compounds of formula (I) in the form of their racemates, racemic mixtures and pure enantiomers, and to the diastereomers and mixtures of compounds of formula (I).

The compounds of formula (I) and their pharmaceutically tolerated salts and physiologically functional derivatives are distinguished by favorable actions on lipid metabolism. The compounds can be employed by themselves, or can be employed in combination with further lipid lowering active compounds. The compounds are suitable for the prophylaxis of disturbances in lipid metabolism and, in a certain currently preferable embodiment, for the treatment of disturbances in lipid metabolism. Specifically, the compounds are suitable for treatment of disturbances in lipid metabolism such as hyperlipidemia. The compounds of formula (I) are also suitable for influencing the serum cholesterol level, and for the prevention and treatment of arteriosclerotic symptoms.

The following experimental data demonstrate the pharmacological activity of the compounds according to the present invention.

Biological testing of the compounds of the present invention was carried out by determining the inhibition of [$^3$H]-taurocholate uptake in brush border membrane vesicles of the ileum of rabbits. The inhibition test was carried out as follows:

1. Preparation of brush border membrane vesicles from the ileum of rabbits

Preparation of brush border membrane vesicles from the intestinal cells of the small intestine was carried out by the so-called $Mg^{2+}$ precipitation method. Male New Zealand rabbits (2 to 2.5 kg of body weight) were sacrificed by intravenous injection of 0.5 ml of T61®, an aqueous solution of 2.5 mg of tetracaine HCl, 100 mg of embutramide and 25 mg of mebezonium iodide. The small intestine was removed and rinsed with ice-cold physiological saline solution. The terminal 7/10 of the small intestine (measured in the oral-rectal direction, i.e., the terminal ileum, which contains the active $Na^+$-dependent bile acid transportation system) was used for preparation of the brush border membrane vesicles. The intestines were frozen at −80° C. in plastic bags under nitrogen.

For preparation of the membrane vesicles, the frozen intestines were thawed at 30° C. in a water-bath. The mucosa was scraped off and suspended in 60 ml of ice-cold 12 mM TRIS/HCl buffer (pH 7.1)/300 mM mannitol, 5 mM EGTA/ 10 mg/l of phenylmethylsulfonyl fluoride/1 mg/l of trypsin inhibitor from soybeans (32 U/mg)/0.5 mg/l of trypsin inhibitor from the bovine lung (193 U/mg)/5 mg/l of bacitracin. After dilution to 300 ml with ice-cold distilled water, the mixture was homogenized with an Ultraturrax (18-rod, IKA Werk Staufen, Germany) at 75% of the maximum for 3 minutes, while cooling with ice. After addition of 3 ml of 1 M $MgCl_2$ solution (final concentration 10 mM), the mixture was left to stand at 0° C. for exactly 1 minute. By addition of $Mg^{2+}$, the cell membranes aggregated, and precipitated with the exception of the brush border membranes. After centrifugation at 3000× g (5000 rpm, SS-34 rotor) for 15 minutes, the precipitate was discarded and the supernatant, which contained the brush border membrane, was centrifuged at 48,000× g (20,000 rpm, SS-34 rotor) for 30 minutes. The supernatant was discarded and the precipitate was rehomogenized in 60 ml of 12 mM TRIS/HCl buffer (pH 7.1)/60 mM mannitol, 5 mM EGTA with a Potter Elvejhem homogenizer (Braun, Melsungen, 900 rpm, 10 strokes). After addition of 0.1 ml of 1 M $MgCl_2$ solution and an incubation time of 15 minutes at 0° C., the mixture was centrifuged again at 3000× g for 15 minutes. The supernatant was then centrifuged again at 48,000× g (20,000 rpm, SS-34 rotor) for 30 minutes. The precipitate was taken up in 30 ml of 10 mM TRIS/HEPES buffer (pH 7.4)/300 mM mannitol and resuspended homogeneously by 20 strokes in a Potter Elvejhem homogenizer at 1000 rpm. After centrifugation at 48,000× g (20,000 rpm, SS-34 rotor) for 30 minutes, the precipitate was taken up in 0.5 to 2 ml of TRIS/HEPES buffer (pH 7.4)/280 mM mannitol (final concentration 20 mg/ml) and resuspended with the aid of a tuberculin syringe with a 27-gauge needle. The vesicles were either used directly for transportation studies after the preparation or stored at −196° C. in 4 mg portions in liquid nitrogen.

2. Inhibition of the $Na^+$-dependent [$^3$H]taurocholate uptake in brush border membrane vesicles of the ileum The uptake of substrates in the brush border membrane vesicles described above was determined by means of the so-called membrane filtration technique. 10 µl of the vesicle suspension (100 µg of protein) were pipetted as drops onto the wall of a polystyrene incubation tube (11×70 mm), which contained the incubation medium with the corresponding ligands (90 µl). The incubation medium comprised 0.75 µl=0.75 µCi [$^3$H(G)]-taurocholate (specific activity: 2.1 Ci/mmol)/0.5 µl of 10 mM taurocholate/8.75 µl of sodium transportation buffer (10 mM TRIS/HEPES (pH 7.4)/100 mM mannitol/100 mM NaCl) (Na-T-B) or 8.75 µl of potassium transportation buffer (10 mM TRIS/HEPES (pH 7.4)/ 100 mM mannitol/100 mM KCl) (K-T-B) and 80 µl of the inhibitor solution in question, dissolved in Na-T buffer or K-T buffer, depending on the experiment. The incubation medium was filtered through a polyvinylidene fluoride membrane filter (SYHV LO 4NS, 0.45 µm, 4 mm Ø, Millipore, Eschborn, Germany). The transportation measurement was started by mixing the vesicles with the incubation medium. The concentration of taurocholate in the incubation batch was 50 µM. After the desired incubation time (usually 1 minute), the transportation was stopped by addition of 1 ml of ice-cold stopping solution (10 mM TRIS/HEPES (pH 7.4)/150 mM KCl). The mixture formed was immediately filtered off with suction under a vacuum of from 25 to 35 mbar over a membrane filter of cellulose nitrate (ME 25, 0.45 µm, 25 mm diameter, Schleicher & Schuell, Dassell, Germany). The filter was rinsed with 5 ml of ice-cold stopping solution.

To measure the uptake of the radioactively labeled taurocholate, the membrane filter was dissolved with 4 ml of the scintillator Quickszint 361 (Zinsser Analytik GmbH, Frankfurt, Germany) and the radioactivity was measured by liquid scintillation measurement in a TriCarb 2500 measuring apparatus (Canberra Packard GmbH, Frankfurt, Germany). The values measured were obtained as dpm (decompositions per minute) after calibration of the apparatus with the aid of standard samples and after correction of any chemiluminescence present.

The control values in each case were determined in Na-T-B and K-T-B. The difference between the uptake in Na-T-B and K-T-B gave the $Na^+$-dependent transportation content. The concentration of inhibitor at which the $Na^+$-dependent transportation content was inhibited by 50%, compared to the control value, was designated the $IC_{50}$ $Na^+$.

The pharmacological data comprise a test series in which the interaction of the compounds according to the invention with the intestinal bile acid transportation system in the terminal small intestine was investigated. The results are summarized in Table 1.

Table 1 shows measurement values of the inhibition of [$^3$H]-taurocholate uptake in brush border membrane vesicles of the ileum of rabbits. The quotients of the $IC_{50Na}$ values of the reference substance as taurochenedeoxycholate (TCDC) and of the particular test substance are shown.

TABLE 1

| Compounds from Example | $IC_{50Na}$-TCDC (µmol)/ $IC_{50Na}$-compound (µmol) |
|---|---|
| 1j | 1.51 |
| 1k | 1.59 |
| 2d | 0.56 |
| 2e | 1.96 |
| 4 | 0.50 |
| 7 | 0.15 |
| 8 | 0.91 |
| 9 | 2.02 |
| 10 | 1.63 |
| 11 | 1.96 |
| 12 | 2.58 |

TABLE 1-continued

| Compounds from Example | IC$_{50Na}$-TCDC ($\mu$mol)/ IC$_{50Na}$-compound ($\mu$mol) |
|---|---|
| 13 | 0.56 |
| 14 | 1.52 |

The following examples serve to illustrate the invention in more detail, without limitation to the products and embodiments described in the examples.

EXAMPLE 1a

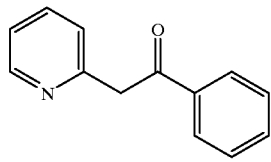

366 ml of 15% strength n-butyllithium in n-hexane were added dropwise to 50 g (0.54 mol) of picoline in 770 ml of tetrahydrofuran at −55° C. The mixture was warmed to room temperature and cooled again to −55° C. 77 g of N,N-dimethylbenzamide (0.52 mol) in 570 ml of tetrahydrofuran were slowly added dropwise and the mixture was then warmed to room temperature and stirred for a further hour. After addition of 550 ml of 1N hydrochloric acid, the mixture was extracted three times with ethyl acetate and the organic phases were dried with MgSO$_4$ and evaporated. Distillation of the residue gave 47.5 g (47%) of product with a boiling point of 134–136° C./0.28 mbar.

EXAMPLE 1b

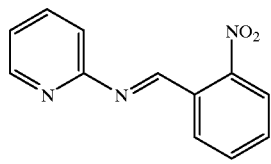

20.0 g (0.13 mol) of o-nitrobenzaldehyde, 12.5 g (0.13 mol) of 2-aminopyridine and 0.3 g of p-toluenesulfonic acid was heated under reflux in 150 ml of toluene for 2.5 hours, using a water separator. The solution was cooled and the precipitate formed was filtered off with suction and dried.

Yield: 18.1 g (60%) of product

Melting point: 93–95° C.

C$_{12}$H$_9$N$_3$O$_2$ (227) MS (FAB) 228 M+H$^+$

EXAMPLE 1c

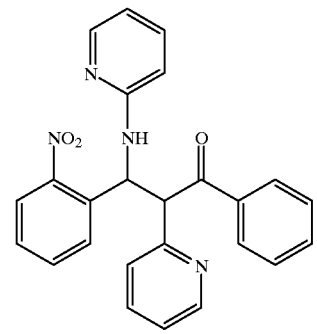

12.0 g (61 mmol) of the ketone from Example 1a and 15.0 g (66 mmol) of the imine from Example 1b were heated on a steam bath for 45 minutes. The reaction mixture was dissolved in ethanol, while heating. After cooling, the precipitate was filtered off with suction and recrystallized from ethanol.

Yield: 11.8 g (46%) of product

C$_{25}$H$_{20}$N$_4$O$_3$ (424.2) MS (FAB) 425 M+H$^+$

EXAMPLE 1d

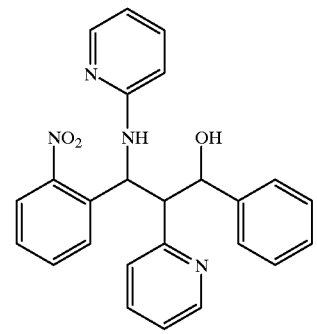

8.0 g (18.8 mmol) of the keto compound from Example 1c were dissolved in 300 ml of tetrahydrofuran/water 10:1, 4.67 g of sodium borohydride were added and the mixture was stirred at room temperature for 2 hours. The solution was then evaporated, 100 ml of 2N hydrochloric acid were added to the residue and the mixture was heated on a steam bath until everything had dissolved. After cooling, the solution was rendered basic with 4N NaOH solution and extracted twice with ethyl acetate. The organic phases were dried with MgSO$_4$ and evaporated. The residue was chromatographed over silica gel (heptane/ethyl acetate 1:1). Two racemic compounds were obtained as the product.

1st fraction: 3.9 g (48%) of nonpolar racemate (Example 1d/1)

C$_2$5H$_{22}$N$_{4O3}$ (426.2) MS (FAB) 427 M+H$^+$

2nd fraction: 2.5 g (31%) of polar racemate (Example 1d/2)

C$_{25}$H$_{22}$N$_4$O$_3$ (426.2) MS (FAB) 427 M+H$^+$

EXAMPLE 1e

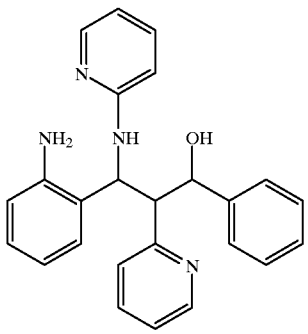

2.5 g (5.86 mmol) of the non-polar racemate from Example 1d/1 were dissolved in 300 ml of methanol, about 20 mg of Pd/C 10% were added and hydrogenation was carried out under an $H_2$ atmosphere at room temperature. The catalyst was filtered off and the solution was evaporated. The residue was chromatographed over silica gel (n-heptane/ethyl acetate 7:13).

Yield: 1.9 g (82%) of product $C_{25}H_{24}N_4O$ (396.22) MS (FAB) 397 M+H[30]

EXAMPLE 1f

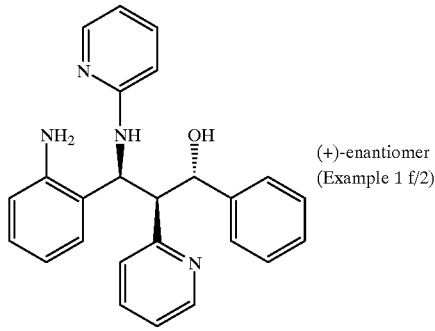

(+)-enantiomer
(Example 1 f/2)

100 mg of the racemic compound from Example 1e were separated into the enantiomers by preparative HPLC. The separation was effected over a CSO-Chiralpak column (Daicel, Duisseldorf) with n-hexane/ethanol 4:1. 40 mg of the (−)-enantiomer (Example 1f/1) were obtained as the 1st fraction and 40 mg of the (+)-enantiomer (Example 1f/2) were obtained as the 2nd fraction.

EXAMPLE 1g

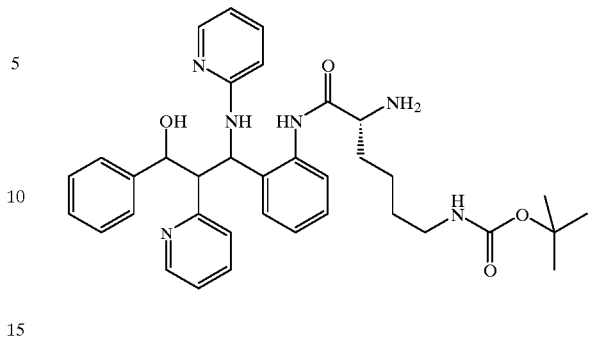

4.0 g (10.1 mmol) of the amino compound from Example 1e (non-polar racemate), 4.85 g (10.3 mmol) of N-Fmoc-D-Lys(BOC)OH, 4.0 g (12.2 mmol) of TOTU and 2.7 ml of triethylamine were dissolved in 300 ml of dimethylformamide and the solution was stirred at room temperature for 2 hours. The reaction mixture was poured onto water and extracted twice with ethyl acetate. The organic phases were dried (MgSO$_4$) and evaporated. The residue was dissolved in 150 ml of dimethylformamide/piperidine 2:1 to split off the Fmoc group and the solution was stirred at room temperature for 1 hour. The solution was then poured onto water and extracted three times with ethyl acetate. The organic phases were dried with MgSO$_4$ and evaporated. Chromatography over silica gel (methylene chloride/methanol 9:1) gave 4.0 g (63.5%) of product.

$C_{36}H_{44}N_6O_4$ (624.3) MS (FAB) 625 M+H[30]

EXAMPLE 1h

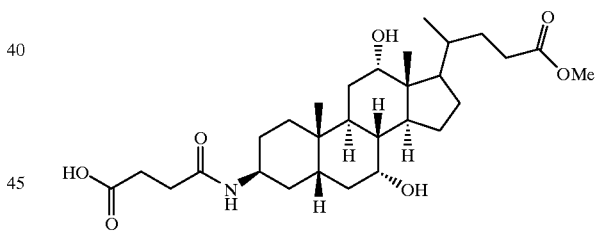

5.0 g (11.86 mmol) of 3β-aminocholic acid methyl ester (European Patent Application EP 0614908), 1.3 g (13 mmol) of succinic anhydride and 16.5 ml of triethylamine were dissolved in 75 ml of tetrahydrofuran and the solution was stirred at room temperature for 1 hour. The solution was evaporated. The residue was dissolved in water and the solution was acidified with hydrochloric acid and extracted three times with ethyl acetate. The organic phases were dried with MgSO$_4$ and evaporated.

Yield: 5.8 g (94%)

$C_{29}H_{47}NO_7$ (521.3) MS (FAB) 528 M+LI$^+$

EXAMPLE 1i

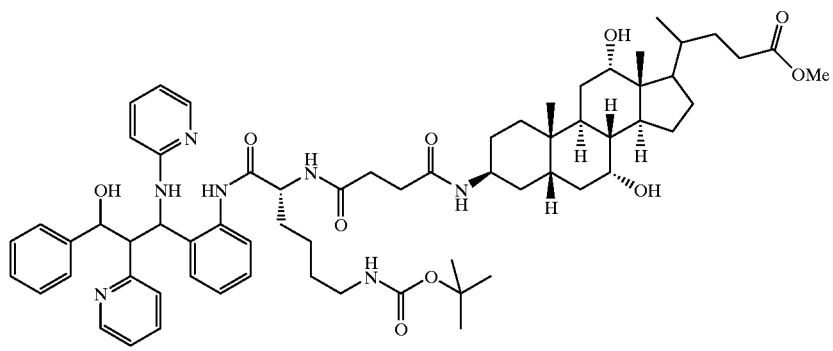

4.0 g (6.4 mmol) of the compound from Example 1g, 3.45 g (6.6 mmol) of the bile acid derivative from Example 1h, 1.2 ml of triethylamine, 2.16 g (16 mmol) of hydroxybenzotriazole and 2.56 g of dicyclohexylcarbodiimide (12.4 mmol) were dissolved in 250 ml of tetrahydrofuran and the solution was stirred at room temperature for 5 hours. The mixture was evaporated, the residue was dissolved in ethyl acetate, and the solution was washed with NaHCO$_3$ solution. The organic phases were dried with MQSO$_4$ and evaporated. Chromatography over silica gel (methylene chloride/methanol 19:1, followed by 9:1) gave 3.1 g (43%) of product.

$C_{65}H_{89}N_7O_{10}$ (1127.7) MS (FAB) 1134.7 M+Li$^+$

EXAMPLE 1j

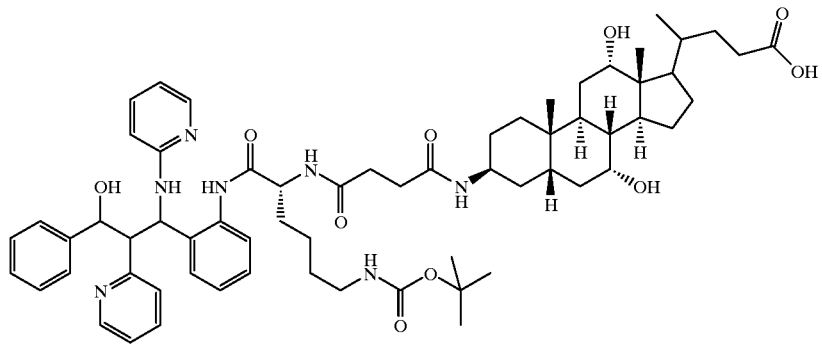

3.1 g (2.75 mmol) of the methyl ester from Example 1i were dissolved in 200 ml of ethanol, 31 ml of 1N NaOH solution were added and the mixture was stirred at room temperature for 5 hours. The mixture was evaporated, the residue was dissolved in water, and saturated NaH$_2$PO$_4$ solution was added. The mixture was extracted twice with ethyl acetate and the organic phases were dried over MgSO$_4$ and evaporated. The crude product was chromatographed over silica gel (methylene chloride/methanol 4:1).

Yield: 2.25 g (73%)

$C_{64}H_{87}N_7O_{10}$ (1113.7) MS (FAB) 1120.7 M+Li$^+$

EXAMPLE 1k

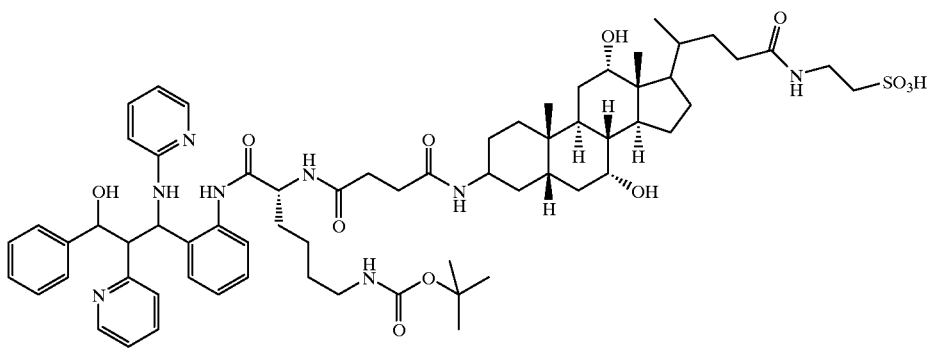

0.48 ml of ethyl chloroformate was added to 1.5 g (1.35 mmol) of the compound from Example 1j and 0.81 ml of triethylamine at 0° C. and the mixture was stirred for 10 minutes. Thereafter, 0.6 g of taurine, dissolved in 30 ml of 0.1 N NaOH solution, was added and the mixture was stirred at room temperature for 24 hours. The mixture was evaporated, the residue was dissolved in a little water and the solution was poured onto saturated $NaH_2PO_4$ solution. The mixture was extracted three times with ethyl acetate and the organic phases were dried with $MgSO_4$ and evaporated. After chromatography over silica gel (methylene chloride/methanol 4:1, followed by methanol), 0.98 g (60%) of taurine conjugate was obtained.

$C_{66}H_{92}N_8O_{12}S$ (1270.7) MS (FAB) 1243.6 M+Na$^+$

EXAMPLE 2a

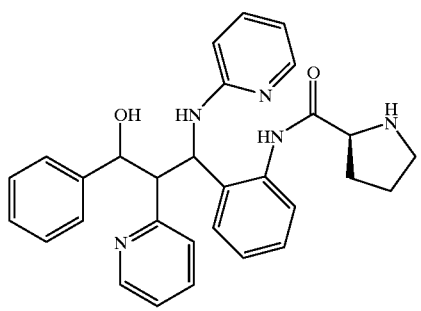

2.5 g (6.31 mmol) of amino compound from Example 1e (non-polar racemate), 2.2 g (6.52 mmol) of Fmoc-L-proline, 2.5 g (7.62 mmol) of TOTU and 1.7 ml of triethylamine were dissolved in 100 ml of dimethylformamide and the solution was stirred at room temperature for 3 hours. The reaction mixture was evaporated to half of its original volume, water was added and the mixture was extracted three times with ethyl acetate. The organic phases were dried over $MgSO_4$ and evaporated. After chromatography over silica gel (ethyl acetate/heptane 7:3), 3.85 g (85%) of product were obtained.

This Fmoc-protected intermediate product (3.6 g) was dissolved in 110 ml of piperidine/DMF 1:10 and the solution was stirred at room temperature for 1 hour. The mixture was evaporated and the residue was chromatographed over silica gel (methylene chloride/methanol 19:1, then 9:1).

Yield: 1.8 g (72.5%)

$C_{30}H_{31}N_5O_2$ (493.2) MS (FAB) 494 M+H[30]

EXAMPLE 2b

Example 2 b/1

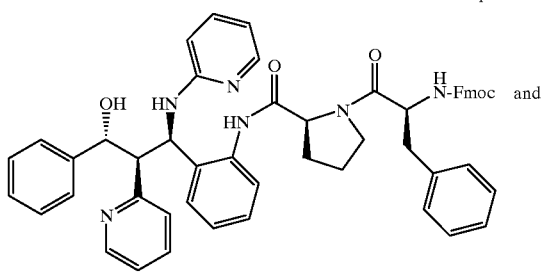

Example 2 b/2

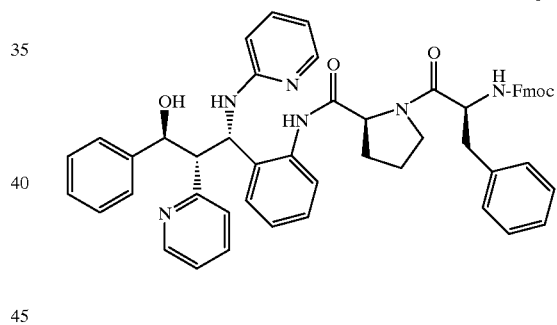

1.7 g (3.44 mmol) of the compound from Example 2a were stirred with 1.4 g (3.61 mmol) of Fmoc-L-phenylalanine, 1.9 g (5.80 mmol) of TOTU and 1.0 ml of triethylamine in 150 ml of DMF at room temperature for 4 hours. The reaction mixture was evaporated and the residue was chromatographed over silica gel (ethyl acetate/n-heptane 4:1). Two fractions were obtained:

1st fraction 1.28 g (43%) of non-polar diastereomer (Example 2b/1)

$C_{54}H_{50}N_6O_5$ (862.4) MS (FAB) 863.4 M+H[30]

2nd fraction 0.82 g (28%) of polar diastereomer (Example 2b/1)

$C_{54}H_{50}N_6O_5$ (862.4) MS(FAB) 863.4 M+H[30]

EXAMPLE 2c

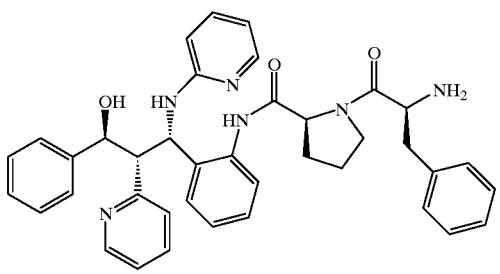

0.8 g (0.93 mmol) of the compound from Example 2b/2 was dissolved in 33 ml of DMF/piperidine 10:1 and the mixture was stirred at room temperature for 1 hour. After evaporation, the residue was chromatographed over silica gel (methylene chloride/methanol 19:1, followed by 9:1).

Yield: 0.35 g (59%).

$C_{39}H_{40}N_6O_3$ (640.3) MS (FAB) 641.3 M+H[30]

EXAMPLE 2d

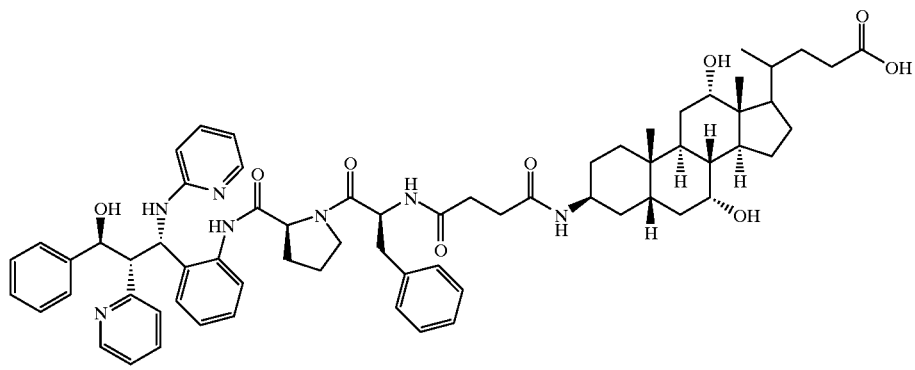

0.5 g (0.78 mmol) of the compound from Example 2c and 0.45 g (0.86 mmol) of the bile acid derivative from Example 1h were reacted by the process described for Example 1i. 0.38 g (43%) of product was obtained.

$C_{68}H_{85}N_7O_9$ (1143.6) MS (FAB) 1144.6 M+H⁺

EXAMPLE 2e 0.31 g (0.27 mmol) of the methyl ester from Example 1d were dissolved in 30 ml of ethanol, 3.0 ml of 1N NaOH solution were added and the mixture was stirred at room temperature for 12 hours. The reaction mixture was evaporated and the residue was chromatographed over silica gel (methylene chloride/methanol 4:1).

Yield: 220 mg (72%)

$C_{67}H_{83}N_7O_9$ (1129.6) MS (FAB) 1130.6 M+H[30]

EXAMPLE 3

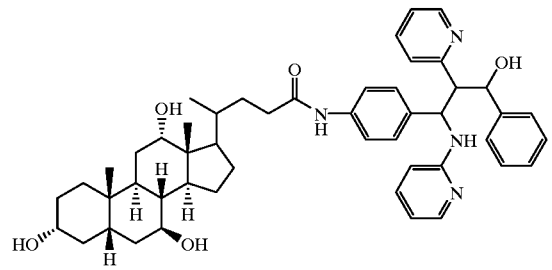

0.3 g (0.78 mmol) of 3-(4-aminophenyl)-1-phenyl-2-pyridin-2-yl-3-(pyridin-2-ylamino)-propan-1-ol (preparation analogously to Example 1e), 0.34 g (0.83 mmol) ursocholic acid, 0.34 g (2.52 mmol) of hydroxybenzotriazole, 0.41 g (2 mmol) of dicyclohexylcarbodiimide and 0.15 ml of triethylamine were stirred in 50 ml of tetrahydrofuran at room temperature for 2 days. When the reaction had ended, the solids were filtered off. The solution was evaporated and the residue was chromatographed over silica gel (methylene chloride/methanol 9:1, followed by 17:3). 0.33 g (55%) of product was obtained.
$C_{49}H_{62}N_4O_5$ (786.5) MS (FAB) 787.5 M+H$^+$
The following examples 4 to 14 were obtained analogously to Examples 1 to 3 starting from the corresponding starting compounds.
EXAMPLE 4
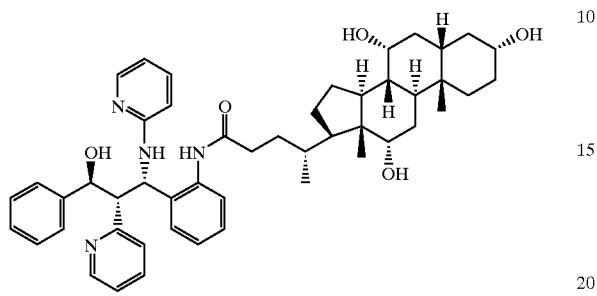
$C_{49}H_{62}N_4O_5$ (787.1) MS (FAB) 788.1 M+H$^+$
EXAMPLE 5
(Non-Polar Diastereomer)
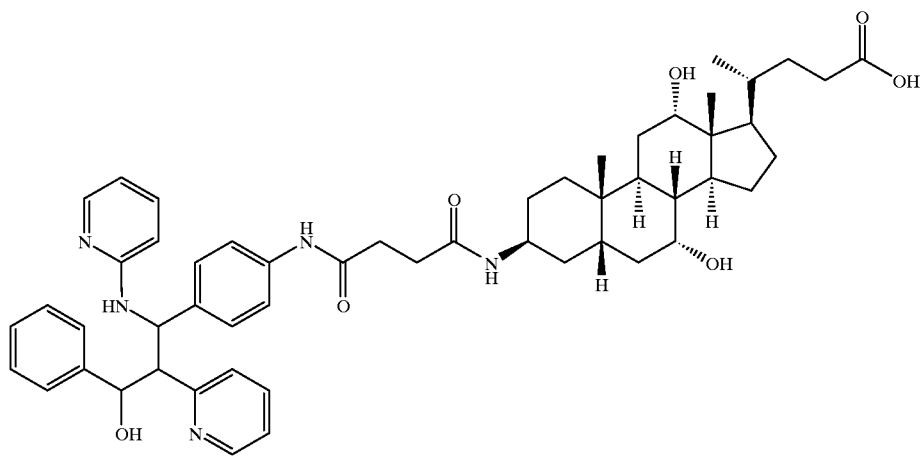

$C_{53}H_{67}N_5O_7$ (886.2) MS (FAB) 887.2 M+H[30]
EXAMPLE 6
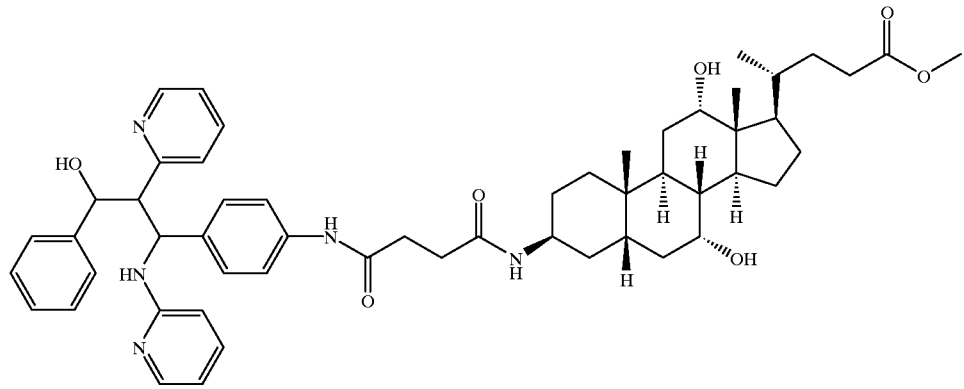
$C_{54}H_{69}N_5O_7$ (900.2) MS (FAB) 901.2 M+H[+]
EXAMPLE 7
(Polar Diastereomer)
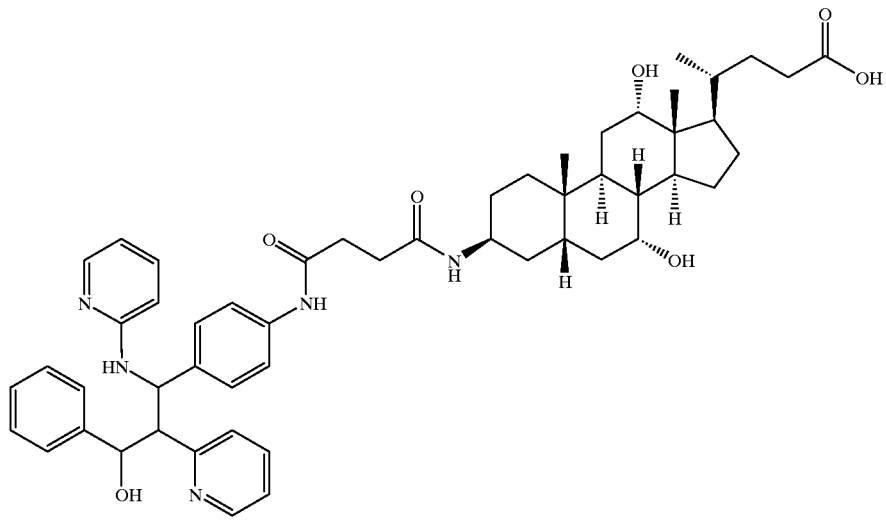

$C_{53}H_{67}N_5O_7$ (886.2) MS (FAB) 887.2 M+H$^+$
EXAMPLE 8
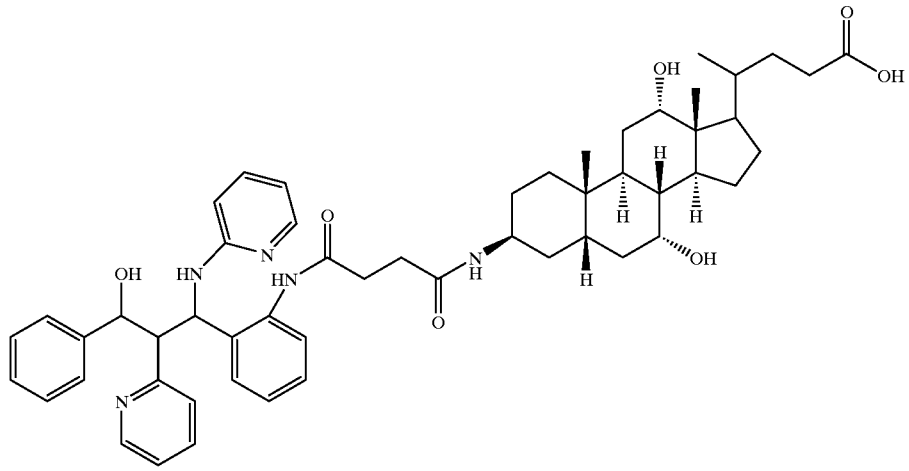
$CH_{67}N_5O_7$ (886.2) MS (FAB) 887.2 M+H$^{30}$
EXAMPLE 9
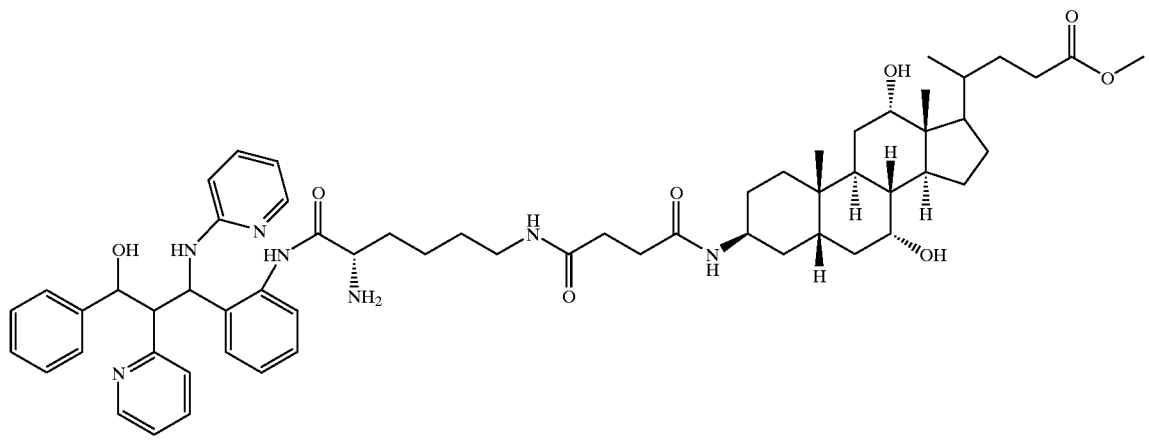

$C_{60}H_{81}N_7O_8$ (1028.4) MS (FAB) 1029.4 M+H$^{30}$
EXAMPLE 10
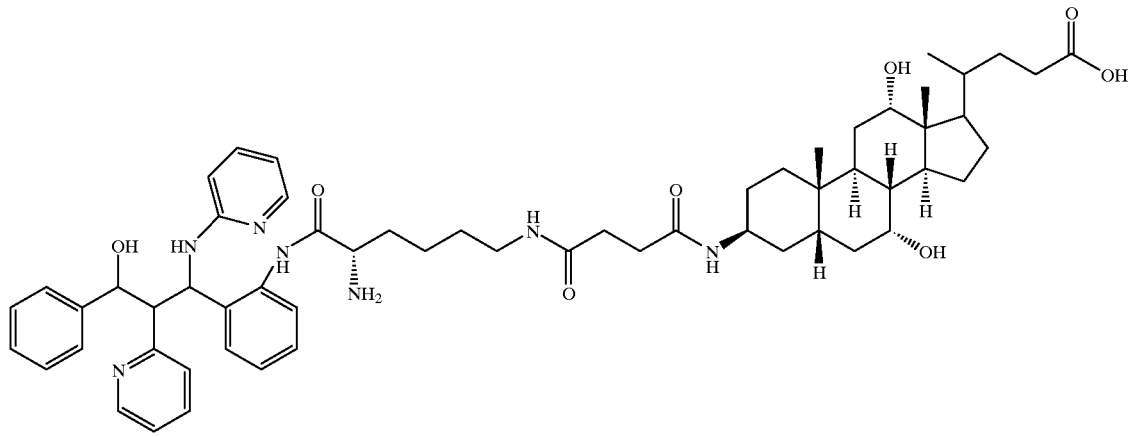
$C_{59}H_{79}N_7O_8$ (1014.3) MS (FAB) 1015.3 M+H$^{30}$
EXAMPLE 11
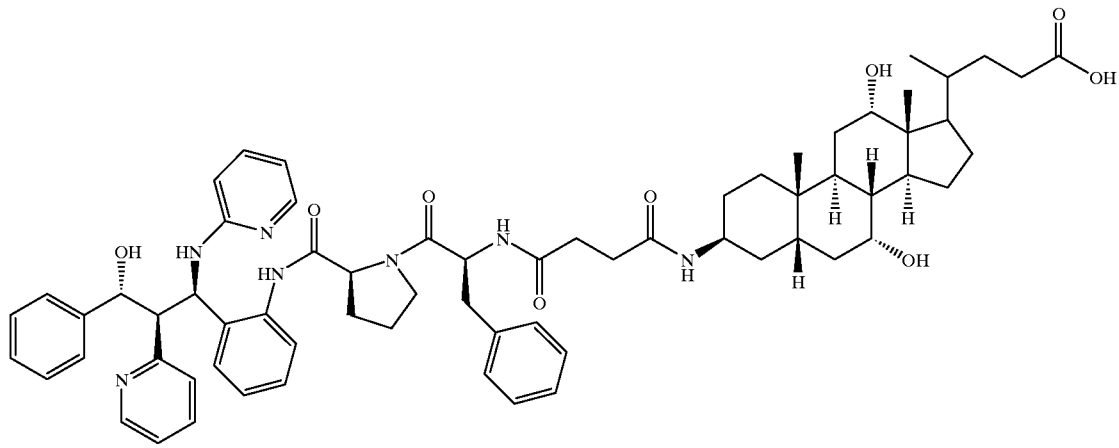

$C_{67}H_{83}N_7O_9$ (1130.5) MS (FAB) 1031.5 M+H[+]
EXAMPLE 12
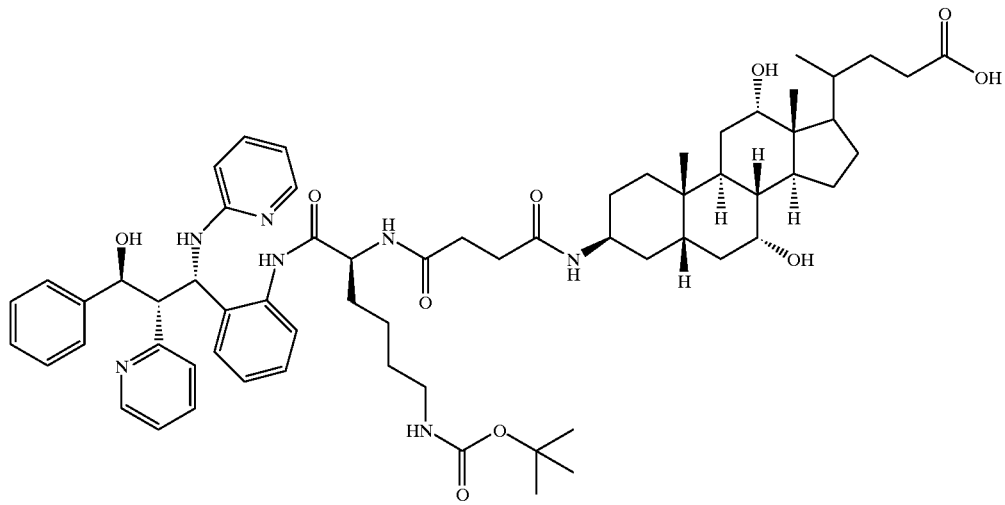
$C_{64}H_{87}N_7O_{10}$ (1114.4) MS (FAB) 1115.4 M+H[+]
EXAMPLE 13
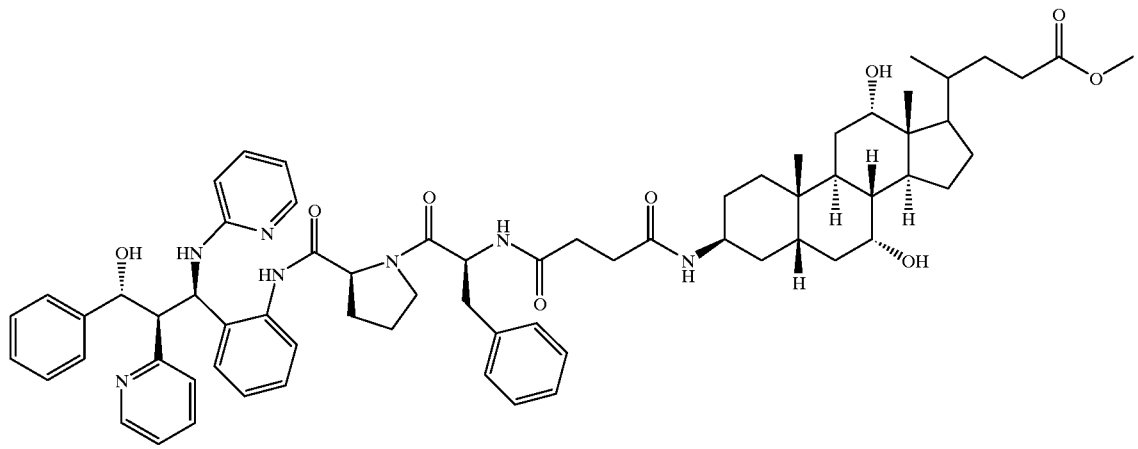

$C_{68}H_{85}N_7O_9$ (1144.5) MS (FAB) 1145.5 M+H[30]

EXAMPLE 14

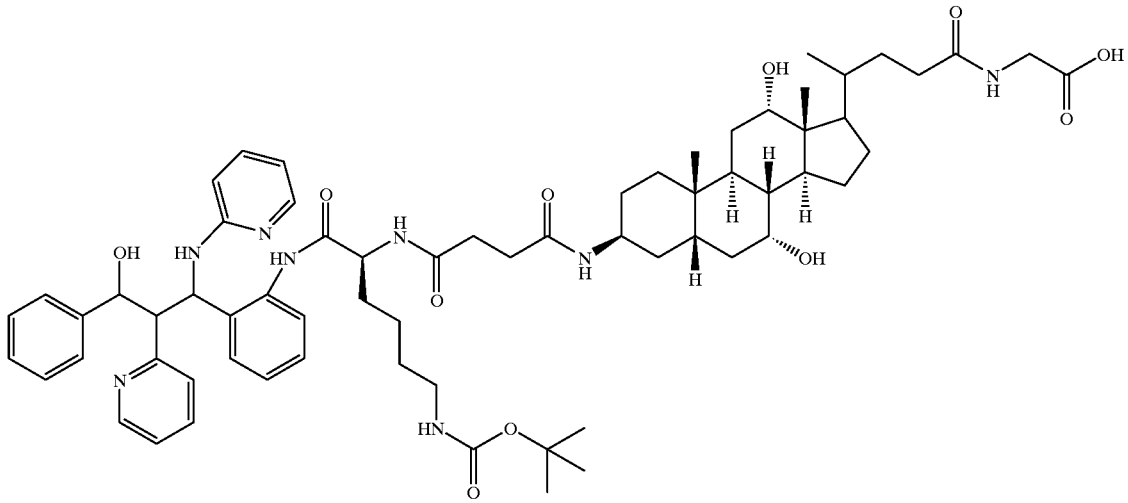

$C_{66}H_{90}N_8O_{11}$ (1171.5) MS (FAB) 1172.5 M+H[30]

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes that come within the meaning and equivalency of the claims are to be embraced within their scope.

We claim:

1. A compound of formula (I)

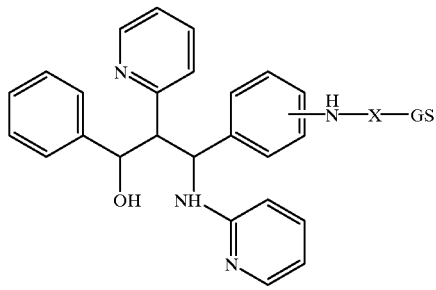

wherein:

GS is a bile acid group of the formula

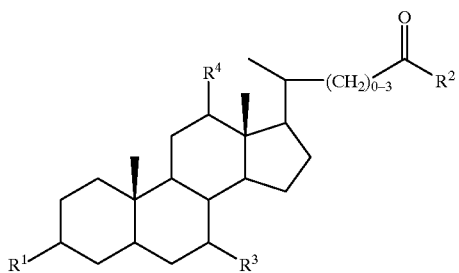

$R^1$ is a bond to X or OH;
$R^2$ is a bond to X, —OH, —O—($C_1$-$C_6$)-alkyl, —NH—($C_2$-$C_6$)-alkyl-$SO_3H$, —N($CH_3$)—$CH_2$—$CH_2$—$SO_3H$, —NH—($C_1$-$C_6$)-alkyl-COOH, or —N($CH_3$)—($C_1$-$C_6$)-alkyl-COOH;
with the proviso that $R^1$ and $R^2$ can not simultaneously be a bond to X;
$R^3$, $R^4$ each independently of one another is H or OH;

X is 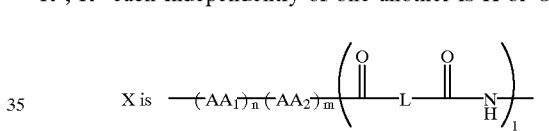

or a bond;
l, m, n each independently of one another is 0 or 1;
L is —($C_1$-$C_6$)-alkyl or phenyl;
$AA^1$, $AA^2$ each independently of one another is an amino acid radical or an amino acid radical which is mono or polysubstituted by an amino acid-protective group;
or a pharmaceutically tolerated salt thereof.

2. A compound of formula (I) as claimed in claim 1, wherein:

GS is a bile acid group of the formula

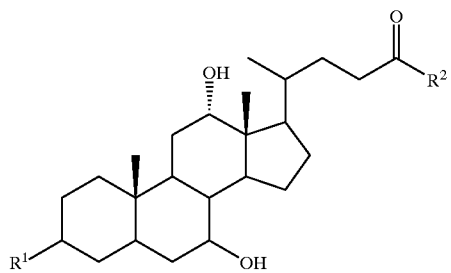

$R^1$ is a bond to X or OH;
$R^2$ is a bond to X, —OH, —O—($C_1$-$C_6$)-alkyl, —NH—($C_2$-$C_6$)-alkyl-$SO_3H$, —N($CH_3$)—$CH_2$—$CH_2$—$SO_3H$, NH—($C_1$-$C_6$)-alkyl-COOH, or —N($CH_3$)—($C_1$-$C_6$)-alkyl-COOH;
with the proviso that $R^1$ and $R^2$ can not simultaneously be a bond to X;

X is 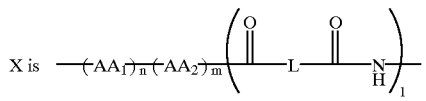

or a bond;

l, m, n each independently of one another is 0 or 1;

L is —(C$_1$–C$_6$)-alkyl or phenyl;

AA$^1$, AA$^2$ each independently of one another is an amino acid radical or an amino acid radical which is mono- or polysubstituted by an amino acid-protective group;

or a pharmaceutically tolerated salt thereof.

3. A compound of formula (I) as claimed in claim 1, wherein:

GS is a bile acid group of the formula

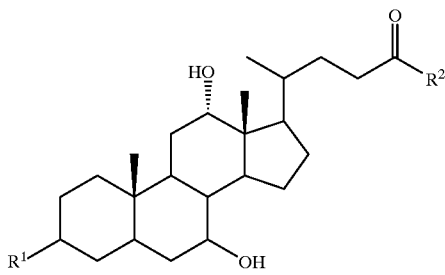

R$^1$ is a bond to X or —OH;

R$^2$ is a bond to X, —OH, —O—(C$_1$–C$_6$)-alkyl, —NH—(C$_2$–C$_6$)-alkyl-SO$_3$H, or —NH—(C$_1$–C$_6$)-alkyl-COOH;

with the proviso that R$^1$ and R$^2$ can not simultaneously be a bond to X;

X is 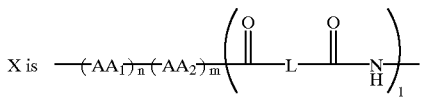

or a bond;

l, m, n each independently of one another is 0 or 1;

L is —(C$_1$–C$_6$)-alkyl;

AA$^1$, AA$^2$ each independently of one another is an amino acid radical or an amino acid radical which is mono- or polysubstituted by an amino acid-protective group;

or a pharmaceutically tolerated salt thereof.

4. A pharmaceutical composition, comprising at least one compound as claimed in claim 1 with a pharmaceutically tolerated excipient.

5. The pharmaceutical composition of claim 4, further comprising at least one additional lipid-lowering active compound.

6. A method of treating disturbances in lipid metabolism, comprising administering to a patient in need thereof an effective amount of a compound as claimed in claim 1.

7. A method of treating hyperlipidemia, comprising administering to a patient in need thereof an effective amount of a compound as claimed in claim 1.

8. A method of treating arteriosclerotic symptoms, comprising administering to a patient in need thereof an effective amount of a compound as claimed in claim 1.

9. A method of treating disturbances in lipid metabolism, comprising administering to a patient in need thereof an effective amount of a compound as claimed in claim 1 in combination with at least one additional lipid-lowering active compound.

10. The method of claim 7, wherein the compound is administered in combination with at least one additional lipid-lowering active compound.

11. The method of claim 8, wherein the compound is administered in combination with at least one additional lipid-lowering active compound.

* * * * *